United States Patent [19]

Park

[11] Patent Number: 5,217,881
[45] Date of Patent: Jun. 8, 1993

[54] HYPERGLYCOSYLATED CYTOKINE CONJUGATES

[75] Inventor: Linda S. Park, Seattle, Wash.

[73] Assignee: Immunex Corporation, Seattle, Wash.

[21] Appl. No.: 827,517

[22] Filed: Jan. 24, 1992

Related U.S. Application Data

[63] Continuation of Ser. No. 343,471, Apr. 25, 1989, abandoned.

[51] Int. Cl.$^5$ ...................... C07K 15/26; C07K 15/14; C12N 15/19; C12N 9/96
[52] U.S. Cl. .................................... 435/69.5; 435/7.5; 435/7.9; 435/69.51; 435/69.52; 435/174; 435/188; 435/964; 436/518; 436/544; 436/545; 436/546; 530/351; 530/395; 530/810
[58] Field of Search .................. 530/351, 395, 810; 435/188, 69.5, 69.51, 69.52, 7.5, 7.9, 174, 964; 436/518, 544, 545, 546

[56] References Cited

U.S. PATENT DOCUMENTS

| | | | |
|---|---|---|---|
| 4,671,958 | 6/1987 | Rodwell et al. | 424/85.91 |
| 5,013,824 | 5/1991 | Abrams et al. | 530/351 |

FOREIGN PATENT DOCUMENTS

WO90/10070  9/1990  World Int. Prop. O. .

OTHER PUBLICATIONS

Hofer et al., Biol. Chem. Hoppe-Seyler 368(9):1060 (1987).
Park et al. (1987) J. Exp. Med. 166:476–488.
Gillis, "TCell Derived Lymphokines," in *Fundamental Immunology*, Second ed. W. E. Paul ed Raven Press Ltd., NY 1989 pp. 621–638.
O'Sullivan et al. (1981) Methods Enzymol 73: 147–165.
Park et al. (1987) J. Exp. Med. 166(2):476–88 Abstract.
Lee et al. (1986) Proc. Natl. Acad. Sci. 83:2061–2065.
Kirkham, J. A. et al., "Stabilisation of Heterologous Proteins in Yeast." *Abstracts of 14th Intl Conf. on Yeast Genetics and Molecular Biology*, S127, 1988.
Price, V. et al., "Expression, purification and characterization of recombinant murine granulocyte-macrophage colony-stimulating factor and bovine interleukin-2 from yeast." *Gene* 55:287–293, 1987.
Brake, A. J. et al., "α-Factor-directed synthesis and secretion of mature foreign proteins in Saccharomyces cerevisiae." *Proc. Natl. Acad. Sci USA* 81: 4642–4646, 1984.
Bitter, G. A. et al., "Secretion of foreign proteins from Saccharomyces cerevisiae directed by α-factor gene fusions." *Proc. Natl. Acad. Sci. USA* 81: 5330–5334, 1984.
Shirakawa, F. et al., "Expression of Interleukin 1 Receptors on Human Peripheral T Cells." *J. of Immunol.* 138:4243–4248, 1987.
Yamasaki, K. et al., "Cloning and Expression of the Human Interleukin-6 (BSF-2/IFNβ2) Receptor." *Science* 241:825–828, 1988.
Hsiao, Humg-Yu and Royer, G. P. "Immobilization of Glycoenzymes through Carbohydrate Side Chains." *Arch. Biochem. Biophys.* 198:379–385, 1979.
Gillis, S. et al., "Production of Recombinant Human Colony Stimulating Factors in Yeast." *Behring Inst. Mitt.* 83:1–7, 1988.
Cosman, D. et al., "Human Interleukin-3 and Granulocyte-Macrophage Colony Stimulating Factor: Site-Specific Mutagenesis and Expression in Yeast." *20th IABS Congress on Cytokines* 69:9–13, 1988.

*Primary Examiner*—Christine M. Nucker
*Assistant Examiner*—Kay K. Kim
*Attorney, Agent, or Firm*—Scott G. Hallquist; Patricia Anne Perkins

[57] ABSTRACT

Ligand reagents are disclosed which consist essentially of recombinant hyperglycosylated cytokines, expressed in yeast, which are purified and conjugated to various functional moieties, for example, biotin groups, via oligosaccharide residues.

10 Claims, 3 Drawing Sheets

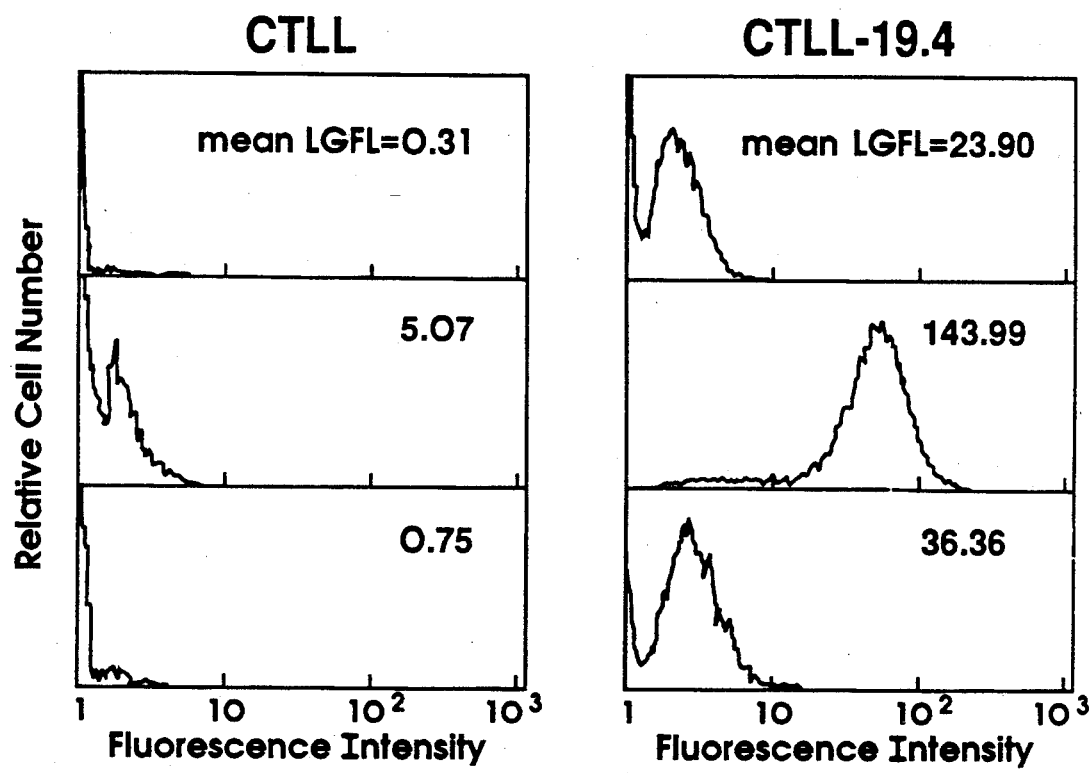
FIGURE 3A  FIGURE 3B

HYPERGLYCOSYLATED CYTOKINE CONJUGATES

This is a continuation of U.S. application Ser. No. 07/343,471, filed Apr. 25, 1989, now abandoned.

BACKGROUND OF THE INVENTION

The present invention relates generally to molecular biology, and particularly to a new class of conjugate ligands based on hyperglycosylated cytokines.

Cytokines are soluble proteins which mediate the hormonal regulation of various cells and tissues. Cytokines deliver a signal to target cells by binding to integral membrane proteins or complexes of proteins, known as receptors. Cytokine receptors contain an extracellular ligand binding region and an intracellular region activated by cytokine binding, which delivers a signal to other intracellular components of the cell. The interaction of cytokines with the extracellular regions of cytokine receptors is highly specific.

Lymphokines are cytokines which regulate and coordinate the activities of various cell types in the immune system. Different immune cells express different populations of lymphokine receptors. For example, T cells, which are involved in the cellular immune response, express varying numbers of interleukin-2 (IL-2) receptors on their cell membranes, depending upon their state of activation. By enumerating the number of cells expressing IL-2 receptors in a particular plasma sample and the average number of receptors per cell, a sensitive assessment can be made of the extent of T-cell activation. Other classes of immune cells express other receptors, for example, receptors for IL-4, IL-3 and IL-1. If the appropriate technology were available, analysis of cytokine receptor expression could be employed as a sensitive tool to enumerate, image or isolate cells in various cell populations or tissue samples. This detection technology could form the basis for new avenues of diagnosis and therapy. For example, certain leukemias are characterized by expression of GM-CSF receptors on the leukemic cells. Such leukemias could be diagnosed and typed by flow cytometry if a reagent capable of detecting GM-CSF receptors were available.

Currently, counting and typing of immune and other circulating blood cells can be conducted by flow cytometry, for example, fluorescence-based cell sorting, wherein laser activation of fluorescent labeling dyes is employed to distinguish cells for separation in an electrostatic field. Flow cytometric apparatus and techniques are well developed, and have been reviewed by Parks and Herzenberg, *Meth. Enzymol.* 108:197 (1984) and Cambier and Monroe, *Meth. Enzymol.* 103:227 (1983). Cells may be labeled for flow cytometry using specific antibody for particular membrane proteins or receptors. In direct immunofluorescence studies, specific antibody is directly conjugated to a fluorescent dye moiety, for example, fluorescein isothiocyanate. In indirect immunofluorescence methods, an unlabeled specific antibody is detected using a labeled antibody which binds the Fc region of the unlabeled antibody.

The use of flow cytometric techniques to detect cytokine receptors is limited by the lack of specific antibodies for most receptors, which is due to the lack of purified receptor (or cell lines expressing high levels of receptor) for immunization. With a few exceptions, e.g., IL-2 receptor (p55 or Tac antigen), preparations of cytokine receptors sufficient to raise specific antibody are not available, due to the low abundance of many receptors on known cell types. For these reasons, biochemical studies of polypeptide hormone receptors have often been limited to indirect methods such as $^{125}I$-ligand crosslinking, due to the combined problems of low receptor abundance and the lack of specific antibody or other molecular probes.

An alternative approach to cytokine receptor detection by flow cytometry using antireceptor antibodies involves labeling the cytokine itself for use as a fluorescence reagent. For example, Shirakawa et al., *J. Immunol.* 138:4243 (1987) disclose labeling of human IL-1α with fluorescein isothiocyanate (FITC) to study the expression of IL-1 receptors on human peripheral T cells. Yamasaki et al., *Science* 241:825 (1988) describe flow cytometric analysis of cells based upon IL-6 receptor expression, using recombinant IL-6 conjugated to biotin, which was then labeled using FITC-avidin. This technique can also be used to purify receptors, based upon the high affinity (Kd $10^{-15}M$) binding of biotinylated polypeptides to avidin and streptavidin for receptor affinity chromatography. One difficulty with this approach is the need to produce a biotinylated ligand which retains the ability to bind to its specific cell surface receptor. The most common approach has been to couple the N-hydroxysuccinimide ester of biotin to primary amines on the protein backbone, e.g., as disclosed by Yamasaki et al. However, if primary amino groups are critical to the receptor-binding function of the ligand, this approach is not feasible. One alternative approach to protein biotinylation involves conjugation to oligosaccharide moieties, which has been demonstrated with immunoglobulins. However, recombinant proteins produced in the most common bacterial expression systems (e.g., *E. coli*) lack glycosylation, and recombinant proteins produced in other systems are glycosylated only to a small extent or to an unpredictably heterogeneous extent.

Another problem in receptor detection by fluorescence-based flow cytometry is low levels of receptor expression. In order to discriminate cells on the basis of receptor expression where receptors are sparsely expressed, for example, at levels of 15-100 receptors per cell, it is necessary to employ a detection reagent which can be labeled with a sufficient number of dye moieties to permit detection of receptor-bearing cells above background levels of fluorescence. To detect receptors which are expressed at levels of 500-1000 receptors per cell requires a reagent with multiple dye residues per ligand. Conventional methods of cytokine labeling, for example, direct FITC-conjugation and FITC-avidin-biotin conjugation, are incapable of providing cytokine reagents with a sufficient number of fluorescein residues to detect many classes of receptors, for example, human GM-CSF and IL-3 receptors. To address these problems, new types of cytokine reagents are needed.

The present invention provides an improved class of cytokine reagents for use in flow cytometry and other receptor-based cell separation techniques in which functional groups, for example, biotin groups, are conjugated to oligosaccharide moieties. The improvement of the present invention resides in the use of recombinant hyperglycosylated cytokines, which are produced in yeast. Yeast are capable of expressing protein having higher levels of O-linked and N-linked mannose (glycosylation) than mammalian cells. The resulting "halo" of polysaccharide on the hyperglycosylated cytokine, which can account for as much as 70% of the weight of the molecule, provides a useful substrate for conjugation of multiple biotin or other linker moieties. Hyperglycosylated cytokines can be labeled to very high specific fluorescence levels without deleteriously affecting the receptor binding characteristics of the conjugate ligand. Hyperglycosylated cytokine conjugates can be employed not only in fluorescence-activated flow cytometry, but also in other analysis, imaging or separation techniques.

SUMMARY OF THE INVENTION

The present invention provides a ligand reagent consisting essentially of a recombinant hyperglycosylated cytokine capable of binding to a cytokine receptor, conjugated to a functional moiety via oligosaccharide residues. In preferred aspects, such hyperglycosylated cytokines are provided by engineering analog cytokines comprising an amino acid sequence which is substantially identical to the amino acid sequence of a naturally occurring cytokine, but wherein the mutant sequence has been altered by the addition, deletion, or substitution of amino acid residues to introduce one or more N-linked glycosylation sites not present in the naturally occurring cytokine. As functional moieties, the conjugates of the present invention can comprise another coupling group, for example biotin, which can be used to couple the conjugate to a third member, for example, an avidin- or streptavidin-linked radiolabel, fluorophore, chromophores, solid substrate, magnetic particle, toxin, enzyme, or another ligand. Alternatively, the conjugate can comprise any of the foregoing functional groups coupled directly.

The present invention also provides various methods of using the ligand reagents of the invention, including methods for detecting cells in a population which express selected cytokine receptors, methods for separating cells from other cells, and methods of purifying cytokine receptor proteins.

BRIEF DESCRIPTION OF THE FIGURES

FIGS. 3A and 3B depict the results of FACS experiments in which an IL-4-fluorescein conjugate was employed to label and detect cells expressing IL-4 receptors, as described in Example 2, below. In FIGS. 3A and 3B "LGFL" means log green fluorescence.

DETAILED DESCRIPTION OF THE INVENTION

Figure 1:
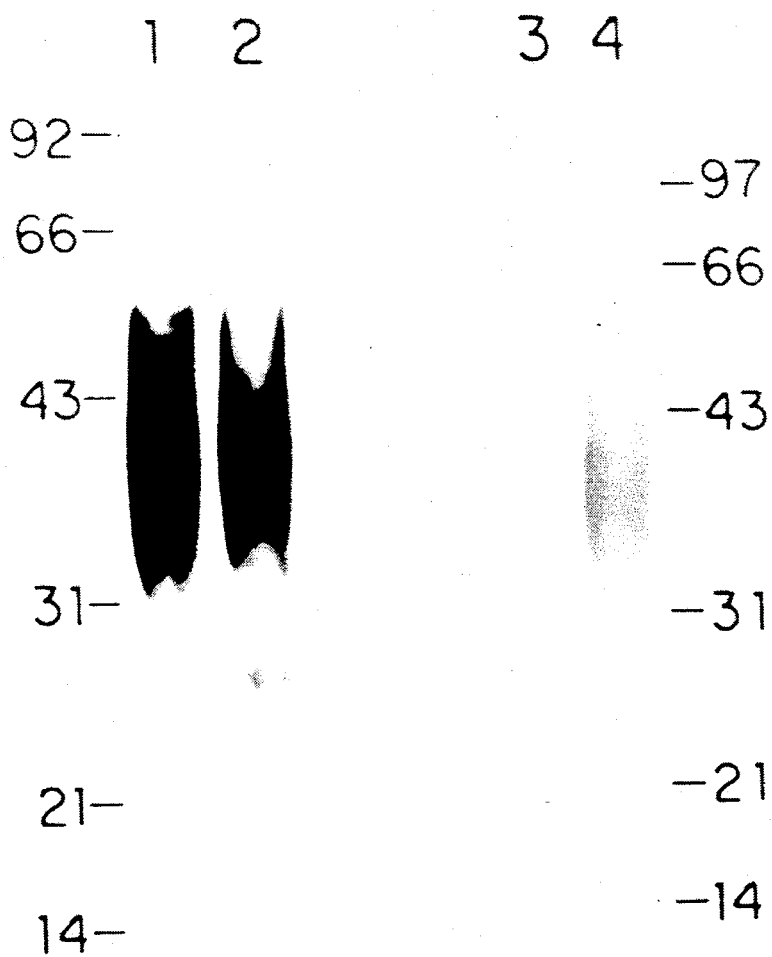
FIG. 1 indicates the result of SDS gel electrophoresis of biotinylated (lanes 2,4) and non-biotinylated (lanes 1,3) hyperglycosylated muGM-CSF prepared as described in Example 1, below. Following electrophoresis, proteins were visualized using silver staining (lanes 1 and 2) or streptavidin peroxidase (lanes 3 and 4).

The heterobifunctional cell discrimination reagents of the present invention are hyperglycosylated recombinant cytokines conjugated to a functional moiety which provides a label, marker, binding reagent, substrate, ligand, or other effector, for example, a toxin.

Expression of recombinant cytokines in the yeast *Saccharomyces cerevisiae* has resulted in production of hyperglycosylated polypeptides which retained biological activity and receptor binding capacity. Studies with IL-3, IL-4, and GM-CSF indicate that the presence of even large amounts of N-linked carbohydrate did not significantly effect the bioactivity of these molecules. Moreover, such hyperglycosylated proteins can be covalently bound to effector groups. For example, hyperglycosylated murine GM-CSF can be conjugated to least 4 moles biotin/mole protein without affecting the ability of the molecule to bind to its receptor. Similar studies with other recombinant yeast-derived cytokines suggest that substantial biotinylation of the carbohydrate region is possible without affecting receptor binding. Where hyperglycosylated polypeptide hormones are available, biotinylation provides a useful procedure for generating biotinylated probes for the analysis of polypeptide hormone receptors.

Cytokines suitable for conjugation to provide the reagents of this invention include naturally glycosylated lymphokines, for example, IL-3, IL-4, IL-5, IL-6, IL-7, GM-CSF, CSF-1, megakaryocyte CSF, erythropoietin, and neuroleukin, which are expressed in yeast to provide additional glycosylation. Other cytokines include growth factors, such as fibroblast growth factor (acidic and basic), various members of the transforming growth factor $\beta$ superfamily, e.g., TGF-$\beta$, bone morphogenetic factor-1, nerve growth factor, platelet derived growth factor (PDGF) and insulin growth factors. For use in preparing the reagents of the present invention, a cDNA encoding a selected cytokine is expressed in recombinant yeast using a suitable yeast expression vector. Hyperglycosylated protein is then isolated and employed to prepare the conjugate reagent. Cytokines which are not naturally glycosylated, for example, IL-1$\alpha$, IL-1$\beta$, IL-2, G-CSF or tumor necrosis factor, must be engineered to include one or more N-glycosylation sites to be employed effectively.

Recombinant proteins secreted by yeast acquire covalently attached carbohydrate units following translation, frequently in the form of oligosaccharide units linked to asparagine side chains by N-glycosidic bonds. Both the structure and number of oligosaccharide units attached to a particular secreted protein can be highly variable, resulting in a wide range of apparent molecular masses attributable to a single glycoprotein. For example, purified mixtures of recombinant glycoproteins such as human or murine granulocyte-macrophage colony-stimulating factor (GM-CSF) can consist of from 0 to 70% carbohydrate by weight.

Preferably, the hyperglycosylated cytokines employed in producing the ligand conjugates of the invention comprise at least about 20% by weight carbohydrate. More preferably, the cytokines comprise at least about 30% by weight sugar, and most preferably, at least about 40% by weight oligosaccharide. RP-HPLC can be employed to isolate protein fractions having the required degree of glycosylation.

Optionally, hyperglycosylated cytokines be prepared by engineering analog cytokines having new glycosylation sites. These analogs are mutant polypeptides which have amino acid sequences altered by addition, deletion, or substitution of amino acid residues to introduce one or more N-linked glycosylation sites not present in the naturally occurring cytokine. N-glycosylation sites in eukaryotic proteins are characterized by the amino acid triplet Asn-X-Z, where X is any amino acid, and Z is Ser or Thr. In this sequence, asparagine provides a side chain amino group for covalent attachment of carbohydrate. Such a site can be added to a cytokine by substituting Asn for another amino acid; substituting Ser or Thr for residue Z where an Asn residue occurs naturally; deleting intermediate residues between existing Asn and Ser or Thr residues; or inserting an amino acid between existing adjacent Asn and Ser or Thr residues. Preferably, substitutions are made conservatively; i.e., the most preferred substitute amino acids are those having physicochemical characteristics resembling those of the residue to be replaced. Moreover, substitutions are not preferred in regions of the cytokine known to be important for receptor-binding activity. Alternatively, hyperglycosylated cytokines can be expressed with N-terminal or C-terminal added sequences in which one to five, or more, N-glycosylation sites are provided.

DNAs encoding analogs are produced by oligonucleotide synthesis and ligation or by site-specific mutagenesis techniques as described in Example 3, below. Mutations can be introduced at particular loci by synthesizing oligonucleotides containing a mutant sequence, flanked by restriction sites enabling ligation to fragments of the native sequence. Alternatively, oligonucleotide-directed site-specific mutagenesis procedures can be employed to provide an altered gene having particular codons altered according to the substitution, deletion, or insertion required. Walder et al., *Gene* 42:133 (1986); Bauer et al., *Gene* 37:73 (1985); Craik, *Biotechniques*, January 1985, 12–19; Smith et al., *Genetic Engineering: Principles and Methods* (Plenum Press, 1981); and U.S. Pat. No. 4,518,584 disclose suitable techniques, and are incorporated by reference herein.

Yeast systems, preferably employing Saccharomyces species such as *S. cerevisiae*, are employed to express DNAs encoding hyperglycosylated cytokines. Generally, useful yeast vectors will include origins of replication and selectable markers permitting transformation of both yeast and *E. coli*, e.g., the ampicillin resistance gene of *E. coli* and *S. cerevisiae* TRP1 gene, and a promoter derived from a highly expressed yeast gene to induce transcription of a downstream structural sequence. Such promoters can be derived from yeast transcriptional units encoding highly expressed genes such as 3-phosphoglycerate kinase (PGK), α-factor, acid phosphatase, or heat shock proteins, among others. The heterologous structural sequence is assembled in appropriate frame with translation initiation and termination sequences, and, preferably, a leader sequence capable of directing secretion of translated protein into the extracellular medium.

Useful yeast vectors can be assembled using DNA sequences from pBR322 for selection and replication in *E. coli* (Amp$^r$ gene and origin of replication) and yeast DNA sequences including a glucose-repressible alcohol dehydrogenase 2 (ADH2) promoter. The ADH2 promoter has been described by Russell et al., *J. Biol. Chem.* 258:2674 (1982) and Beier et al., *Nature* 300:724 (1982). Such vectors may also include a yeast TRP1 gene as a selectable marker and the yeast 2μ origin of replication. A yeast leader sequence, for example, the α-factor leader which directs secretion of heterologous proteins from a yeast host, can be inserted between the promoter and the structural gene to be expressed. See Kurjan et al., U.S. Pat. No. 4,546,082; Kurjan et al., *Cell* 30:933 (1982); and Bitter et al., *Proc. Natl. Acad. Sci. USA* 81:5330 (1984). The leader sequence may be modified to contain, near its 3' end, one or more useful restriction sites to facilitate fusion of the leader sequence to foreign genes.

Suitable yeast transformation protocols are known to those of skill in the art; an exemplary technique is described by Hinnen et al., *Proc. Natl. Acad. Sci. USA* 75:1929 (1978), selecting for Trp$^+$ transformants in a selective medium consisting of 0.67% yeast nitrogen base, 0.5% casamino acids, 2% glucose, 10 μg/ml adenine and 20 μg/ml uracil.

Host strains transformed by vectors comprising the ADH2 promoter may be grown for expression in a rich medium consisting of 1% yeast extract, 2% peptone, and 1% glucose supplemented with 80 μg/ml adenine and 80 μg/ml uracil. Depression of the ADH2 promoter occurs upon exhaustion of medium glucose. Crude yeast supernatants are harvested by filtration and held at 4° C. prior to further purification.

Purification of hyperglycosylated cytokines is conveniently accomplished by single or sequential reversed-phase high performance liquid chromatography procedures (RP-HPLC) on a preparative HPLC column, by methods analogous to those described by Urdal et al., *J. Chromatog.* 296:171 (1984), and Grabstein et al., *J. Exp. Med.* 163:1405 (1986). Hydrophobic RP-HPLC media, e.g., silica gel having pendant methyl or other aliphatic groups, is useful to purify a hyperglycosylated composition.

For example, yeast-conditioned medium containing a glycosylated cytokine can be filtered through a 0.45μ filter and initially purified by batch adsorption and elution from a cation exchange matrix, for example, S-Sepharose. Pooled fractions from the batch adsorption/elution step can then be pumped, at a flow rate of 100 ml/min, onto a 5 cm×30 cm column packed with 10–20μ reversed phase silica (Vydac, The Separations Group, Hesperia, CA, USA). The column can be equilibrated in 0.1% trifluoroacetic acid in water prior to the application of the yeast-conditioned medium and then flushed with this solvent following application of the medium to the column until the optical absorbance at 280 nm of the effluent approaches baseline values. At this time, a gradient of 0.1% trifluoroacetic acid in acetonitrile can be established that leads from 0 to 60–100% Solvent B at a rate of change of 1–2% per minute and at a flow rate of 100 ml/min. At a suitable time (10–20 minutes) following initiation of the gradient, one minute fractions are collected and aliquots of the fractions analyzed for protein content by polyacrylamide gel electrophoresis and fluorescamine protein determination. Additional HPLC or ion-exchange chromatographic steps can be employed if indicated.

Engineered cytokines comprising the amino acid sequence DYKDDDDK (See Example 3) can be directly purified using specific antibody, as described in U.S. Pat. No. 4,703,004.

Following purification, the cytokines are conjugated to other functional groups by methods known to those of skill in the art. One approach involves periodate oxidation of carbohydrate side chains to provide aldehyde groups, which are then reacted with biotin hydrazide to conjugate biotin groups to the oxidized carbohydrate moieties. The resulting biotinylated reagent can then be linked to various avidin- or streptavidin-conjugated reagents, for example, FITC-avidin or avidin-agarose. Fluorescein groups can also be conjugated to periodate-oxidized carbohydrate groups using the reagent (((2(carbohydrazino)methyl)-thio)acetyl)-aminofluorescein, as described in Example 3, below. Alternatively, periodate-oxidized protein can be reacted with reagents which provide spacer groups, for example, ethylenediamine or glycyltyrosine, to generate adducts suitable for coupling to CNBr-activated agarose or an aminocaproate adduct of agarose via an N-hydroxysuccinimide ester, or to other functional groups such as proteins using analogous methods. Useful techniques are reviewed by Ghose et al., *Methods Enzmol.* 93:280 (1983) and O'Sullivan and Marks, *Methods Enzmol.* 73:147 (1981).

The various methods of use of the reagents of the invention include methods in which cells in a population of cells are detected using the reagents of the invention. Depending upon the nature of the functional moiety, various detecting means can be employed, for example, radiometric, laser-activated fluorescent, photographic, magnetic, or others. Optionally, cells can be separated following detection, for example, by flow cytometry in a fluid stream. In another approach, avidin-coated magnetic particles can be used to select cells which have bound a biotin-conjugated hyperglycosylated cytokine, which are then concentrated or separated using a magnetic field. Avidin can be covalently bound to silanized ferromagnetic particles by carbodiimide, glutaraldehyde or diazotization methods, using methods analogous to those disclosed by U.S. Pat. No. 4,672,040.

Alternatively, the detected cells may be enumerated or imaged in planar sections of tissue which are contacted with a labeled cytokine conjugate. In the latter approach, a radiolabeled conjugate can be employed which is imaged using photographic or X-ray film, optionally with an image intensifier.

Other methods of interest include methods for diagnosis of particular physiological or pathological conditions, comprising detecting cells in a population which express selected cytokine receptors, using the reagents of the invention. As an example, a panel of cytokine receptor detection reagents can be employed to provide a profile of cell types in the population. Finally, methods for therapy of particular physiological or pathological conditions can be based upon the reagents of the invention, in which cells expressing selected cytokine receptors are detected and separated from plasma or other body fluid, either by killing the cells or physically removing them from the plasma or fluid and returning the plasma or fluid to the patient. If enrichment of a particular cell population is sought, cells expressing particular receptors can be separated from plasma, expanded ex vivo in the presence of one or more growth factors, and reintroduced to the host.

In addition, as detailed in Example 1, below, the reagents of the invention can be used to purify cytokine receptor proteins by affinity chromatography. In general, such methods comprise contacting a composition comprising the cytokine receptor protein with a ligand reagent of the invention which is conjugated to a solid substrate, in order to bind the cytokine receptor protein to the substrate via the ligand reagent. The resulting bound receptor protein can then be separated from the other components of the composition by elution from a chromatographic column, centrifugation, phase separation, or other methods. Optionally, receptor can be solubilized from whole cell preparations using a detergent, for example, CHAPS, Nonidet NP-40, or SDS/.

EXAMPLE 1

Preparation and Use of Biotinylated Hyperglycosylated GM-CSF to Detect GM-CSF Receptors In the following series of experiments, glycosylated recombinant murine GM-CSF was specifically biotin-labeled on the carbohydrate portion by treatment with periodate followed by biotin hydrazide. Biotinyl-GM-CSF bound to specific receptors of LSTRA cells with an affinity identical to underivatized hormone, and was used to affinity purify the GM-CSF receptor from the cells by adsorption to avidin agarose or Affigel, and the receptor specifically eluted by destabilizing the binding of GM-CSF to its receptor with octylglucoside.

GM-CSF is a polypeptide hormone which controls the growth, differentiation, and survival of hematopoietic progenitor cells. GM-CSF stimulates proliferation of granulocytes and macrophages. Like other polypeptide hormones, GM-CSF initiates its cellular activity by binding to specific high affinity receptors on the surface of responding cells. Binding studies with $^{125}$I-labeled GM-CSF have shown that murine cells of both myelomonocytic and T-cell origin generally display a single class of high affinity receptors (1000-5000 receptors/cell) with a $K_a$ of $10^8$-$10^9 M^{-1}$. GM-CSF receptors are present on human cells at significantly lower levels (100-500 receptors/cell) and bind GM-CSF with a $K_a$ of $10^9$-$10^{11} M^{-1}$.

Biochemical characterization of the GM-CSF receptor has thus far been limited to crosslinking studies which have produced inconsistent results. The following experiment demonstrates the successful detection of surface-labeled murine GM-CSF receptor using a novel approach in which the hyperglycosylation of recombinant murine GM-CSF, produced in a yeast expression system, was exploited to produce a fully active biotinylated hormone analog.

Biotin was attached to the carbohydrate portion of the hyperglycosylated form of rmuGM-CSF (containing $M_r$ 25,000 of carbohydrate) by periodate oxidation of sugar residues followed by treatment with biotin hydrazide. The resulting biotinylated GM-CSF was capable of binding avidin following gel electrophoresis and western transfer. GM-CSF treated under identical conditions with the omission of periodate oxidation bound no detectable avidin. The biotinyl-GM-CSF contained 4 moles of accessible biotin per mole of GM-CSF as determined by an avidin binding assay, although this value is likely to be an underestimate of total biotin incorporation because of the inherent limitations on avidin binding due to steric hindrance. The ability of biotinyl and underivatized GM-CSF to complete for $^{125}$I-GM-CSF binding to LSTRA cells was compared. The results indicated that incorporation of biotin into the carbohydrate moiety had no effect on the ability of GM-CSF to bind to its receptor. Furthermore, biotinyl-GM-CSF bound to its receptor on LSTRA cells was still accessible to streptavidin as assessed by binding of $^{125}$I-streptavidin.

Recombinant murine GM-CSF (rmuGM-CSF) was expressed in yeast under the control of the alcohol dehydrogenase 2 promoter, and purified from the yeast medium to homogeneity by reverse-phase HPLC as described by Price et al., *Gene* 55:287 (1987). Briefly, purification was achieved by two sequential reverse-phase HPLC steps of C4 and C18 derivatized silica (Vydac, Separations Group) first with a gradient of acetonitrile containing 0.1% trifluoroacetic acid (TFA) and second with a gradient of 1-propanol (60% 1-propanol in 0.9M acetic acid, 0.2M pyridine pH 4). Distinct molecular forms of rmuGM-CSF containing varying levels of glycosylation can be resolved by this purification scheme. For biotinylation, fractions containing hyperglycosylated muGM-CSF with an average $M_r$ of 40,000 were pooled and subjected to a third HPLC step on C4 derivatized silica for solvent exchange to acetonitrile/$H_2O$ in 0.1% TFA. Following purification, protein concentrations were determined by amino acids analysis.

Aliquots (300 µg in 100 µl) of purified hyperglycosylated rmuGM-CSF in acetonitrile/$H_2O$/0.1% TFA were combined with 300 µl of citrate-phosphate buffer (0.1M, pH 5.5) and the acetonitrile evaporated under nitrogen to a final volume of 300 µl. Thirty µl of 10 mM sodium m-periodate, freshly prepared in citrate-phosphate buffer, were added and the mixture incubated at 4° C. for 30 minutes in the dark. The reaction was quenched with 30 µl of 0.1M glycerol and dialyzed for 18 hours at 4° C. against citrate-phosphate buffer. Following dialysis, an equal volume of 10 mM biotin hydrazide, freshly prepared in citrate-phosphate buffer, was added to the sample and incubated at 25° C. for 30 minutes. The GM-CSF-biotin was then exhaustively dialyzed at 4° C. against phosphate buffered saline (0.15M NaCl, 0.05M sodium phosphate, pH 7.4) and the protein concentration determined by amino acid analysis. The final product was analyzed by SDS-polyacrylamide gel electrophoresis and western blotting as described below and avidin-accessible biotin determined according to the method of Green, *Meth. Enzymol.* 18:414 (1970).

Figure 2:
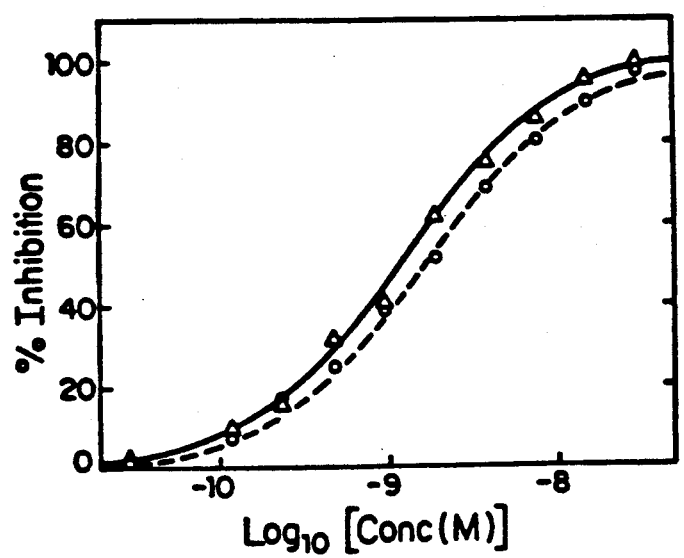
FIG. 2 depicts the results of a binding experiment in which the ability of biotinylated (triangles) and non-biotinylated (circles) hyperglycosylated muGM-CSF to bind to LSTRA cells were compared.

To compare derivatized and underivatized material by SDS-PAGE, aliquots of biotinylated rmuGM-CSF prepared as described above, as well as an underivatized sample prepared by an identical protocol except for the omission of sodium M-periodate, were analyzed on a linear 10–20% gradient gel. As shown in FIG. 1, proteins were visualized following electrophoresis by either silver staining (lanes 1 and 2) or staining with streptavidin peroxidase following transfer to nitrocellulose (lanes 3 and 4). Lanes 1 and 3 contained underivatized material, lanes 2 and 4 contained biotinylated rmuGM-CSF. FIG. 2 depicts the results of binding experiments in which the ability of biotinylated (triangles) and non-biotinylated (circles) hyperglycosylated muGM-CSF to bind to LSTRA cells were compared. In these experiments, LSTRA cells ($1.3 \times 10^7$ cells per ml) were incubated with $^{125}$I-GM-CSF ($7 \times 10^{-10}$M) and varying concentrations of underivatized and biotinylated rmuGM-CSF. Samples were incubated for 45 minutes at 37° C. and binding determined as described by Dower et al., *J. Immunol.* 132:751 (1984). All data were corrected for nonspecific binding measured in the presence of $8.0 \times 10^{-8}$M unlabeled muGM-CSF. The results depicted in FIG. 2 indicate no detectable difference between derivatized and underivatized muGM-CSF.

To purify GM-CSF receptors, cell surface proteins on LSTRA cells ($10^7$–$10^8$) were radiolabeled with $^{125}$I by the glucose oxidase lactoperoxidase method of Cosman et al., *Mol. Immunol.* 23:935 (1986). Labeled cells were washed three times in PBS, two times in binding medium, and incubated at $10^7$ cells/ml with 10–40 nM biotinyl-GM-CSF in binding medium for 30 minutes at 37° C. All subsequent operations were performed at 4° C. Cells were harvested, washed two times with binding medium and three times in PBS to first remove unbound biotinyl-GM-CSF and then to remove the free biotin in binding medium. Cells were resuspended in PBS with protease inhibitors at $10^7$ cells/ml and extracted by adding an equal volume of 1% (w/v) CHAPS in PBS with protease inhibitors, followed by gentle agitation for 40 minutes. After centrifugation at $12,000 \times G$ for 10 minutes, 10 ml of the supernatant was added to 200 µl of avidin agarose or streptavidin Affigel and gently mixed for 2 hours. The agarose or Affigel was pelleted and the supernatant transferred to a second aliquot of gel for 16 hours. The gel was washed exhaustively with 0.5% (w/v) CHAPS in PBS with proteases inhibitors and the receptor eluted by agitation with 200 µl of 3% octylglucoside in PBS with protease inhibitors for 4–16 hours. Subsequently the gel was eluted with 1% Nonidet P40, 1% sodium deoxycholate, 0.1% sodium dodecyl sulfate (SDS), 150 mM NaCl, 50 mM tris-HCl, pH 7.5 (RIPA buffer), and/or SDS sample buffer, which resulted in recovery of detectable quantities of GM-CSF receptors.

EXAMPLE 2

Fluorescence Activated Cell Sorting Using Hyperglycosylated Murine IL-4 Reagent

In the following experiment, cells of the murine T-cell line CTLL (ATCC TIB 214) were sorted using fluorescence activated cell sorting (FACS) and fluorescein conjugated rmuIL-4 prepared as follows. As shown in FIG. 3, sorting provided higher levels of IL-4 receptor expression, to facilitate studies of the murine IL-4 receptor.

Complementary DNA encoding murine IL-4 was cloned from a cDNA library that had been prepared from sized mRNA isolated from EL-4 murine thymoma cells previously stimulated with phorbol myristate acetate (PMA). The IL-4 cDNA was inserted into a yeast expression plasmid substantially similar to that described by Price et al., *Gene* 55:287 (1987), where its transcription, translation and secretion were under the control of the ADH2 promoter and α-factor leader sequence. As a result, yeast transformed with this plasmid secreted murine IL-4 into the yeast culture broth. Purification of IL-4 was achieved by five sequential reversed phase HPLC steps on C4 and C18 derivatized silica (Vydac, separations group) with gradients of acetonitrile containing 1% trifluoroacetic acid or n-propanol (60% n-propanol in 0.9M acetic acid, pyridine to pH 4.5) as previously described for the purification of other lymphokines (Stern et al., *Proc. Natl. Acad. Sci.USA* 81:871, 1984, Urdal et al., *J. Chromatog.* 296:171, 1984, and Watson et al., *J. Immunol.* 137:854, 1986). Following purification, muIL-4 concentrations were determined by amino acid analysis. IL-4 activity was measured in either a B-cell or an FDC-P2 proliferation assay as previously described by Grabstein et al., *J. Exp. Med.* 163:1405 (1986). The specific activity of the resulting purified rmuIL-4 was determined to be $2 \times 10^5$ U/mg. This product exhibited a heterogeneous molecular weight due to yeast glycosylation on SDS-PAGE of about 49,700 daltons, plus or minus 4300, suggesting that approximately 70% of the preparation could be accounted for as oligosaccharide, since the deduced molecular weight of non-glycosylated mature muIL-4 is approximately 14,000.

Aliquots of the resulting hyperglycosylated rmuIL-4 (300 µg in 300 µl of 0.1M citrate-phosphate buffer, pH 5.5) were combined with 30 µl of 10 mM sodium m-periodate (Sigma), freshly prepared in 0.1M citrate-phosphate, pH 5.5, and the mixture was incubated at 4° C. for 30 min in the dark. The reaction was quenched with 30 µl of 0.1M glycerol and dialyzed for 18 hours at 4° C. against 0.1M citrate-phosphate pH 5.5. Following dialysis, a 1/10 volume of 100 mM 5-(((2(carbohydrazino)methyl)thio)acetyl)-aminofluorescein (Molecular Probes, Eugene OR) dissolved in dimethyl sulfoxide (DMSO) was added to the sample and incubated at 25° C. for 30 min. The IL-4-fluorescein was then exhaustively dialyzed at 4° C. against PBS, pH 7.4 and protein concentration determined by amino acid analysis. The final product was stored at 4° C. following the addition of 1% (w/v) BSA and sterile filtration.

For cell sorting, CTLL cells ($5 \times 10^6$) were incubated for 30 min at 37° C. in 150 μl PBS+1% BSA containing 4,546,082). An Asp718 restriction site was introduced at position 237 in the α-factor signal peptide to facilitate fusion to heterologous genes. This was achieved by changing the thymidine residue at nucleotide 241 to a cytosine residue by oligonucleotide-directed in vitro mutagenesis as described by Craik, Biotechniques, January 1985, 12-19. A synthetic oligonucleotide containing multiple cloning sites and having the following sequence was inserted from the Asp718 site at amino acid 79 near the 3' end of the α-factor signal peptide to a SpeI site in the 2μ sequence:

```
Asp718                                              StuI    NcoI   BamHI
GTACCTTTGGATAAAAGAGACTACAAGGACGACGATGACAAGAGGCCTCCATGGAT...
  GAAACCTATTTTCTCTGATGTTCCTGCTGCTACTGTTCTCCGGAGGTACCTA...
                                                    |←—Polylinker—

SmaI          SpeI
...CCCCCGGGACA
...GGGGGCCCTGTGATC
  ———Polylinker———>|
```

$1 \times 10^{-9}$M IL-4-fluorescein under sterile conditions. The mixture was chilled to 4° C., washed once in a large volume of PBS+1% BSA and sorted using an EPICS C flow cytometer (Coulter Instruments). The cells providing the highest level fluorescence signal (top 1.0%) were collected in bulk and the population expanded in liquid cell culture. Following several rounds of sorting, clones were selected which expressed IL-4 receptors at high levels. FIG. 3 shows the results of FACS experiments using the IL-4-fluorescein reagent and parent CTLL cells and one clone (CTLL 19.4) which was isolated using repeated FACS sorting. As shown in the middle panels of FIG. 3, the CTLL 19.4 cell line expresses significantly greater numbers of IL-4 receptors, as indicated by increased binding of IL-4-fluorescein.

EXAMPLE 3

Expression of a Hyperglycosylated Human IL-2 Mutant Protein

In order to produce a human IL-2 protein having increased levels of N-linked carbohydrate for biotinylation, two approaches to mutagenesis were evaluated. In the first approach, a cDNA insert encoding the amino acid sequence of mature human IL-2 (see U.S. Pat. No. 4,738,927) was altered by in-vitro mutagenesis to encode a threonine residue at position 73 of the mature sequence in place of the native alanine residue. In the second approach, a short sequence including two additional N-glycosylation sites and the identification peptide DYKDDDDK was added to the N-terminus of the mature huIL-2 molecule.

To create huIL-2(Thr$^{73}$), a huIL-2 cDNA was first engineered into the yeast expression vector pIXY120 as follows. pIXY120 is identical to pYaHuGM (ATCC 53157), except that it contains no cDNA insert and includes a polylinker/multiple cloning site with an NcoI site. This vector includes DNA sequences from the following sources: (1) a large SphI (nucleotide 562) to EcoRI (nucleotide 4361) fragment excised from plasmid pBR322 (ATCC 37017), including the origin of replication and the ampicillin resistance marker for selection in E. coli; (2) S. cerevisiae DNA including the TRP-1 marker, 2μ origin of replication, ADH2 promoter; and (3) DNA encoding an 85 amino acid signal peptide derived from the gene encoding the secreted peptide α-factor (See Kurjan et al., U.S. Pat. No.

pBC120 also varies from pYaHuGM by the presence of a 514 bp DNA fragment derived from the single-stranded phage f1 containing the origin of replication and intergenic region, which has been inserted at the NruI site in the pBR322 sequence. The presence of an f1 origin of replication permits generation of single-stranded DNA copies of the vector when transformed into appropriate strains of E. coli and superinfected with bacteriophage f1, which facilitates DNA sequencing of the vector and provides a basis for in vitro mutagenesis according to the method of Walder et al, supra.

To introduce a new N-linked glycosylation site into the human IL-2 amino acid sequence, an EcoRI-SpeI fragment from a vector substantially identical to pIXY120 (but lacking the f1 origin) and comprising the human IL-2 cDNA was ligated to EcoRI and SpeI-cut pIXY120 DNA. Plasmid DNA bearing the ligated insert was isolated and used to transform E. coli strain JM107, which was superinfected with helper phage IR1. Single-stranded DNA was isolated and annealed to the mutagenic oligonucleotide 5'-GCTAAATTTAAC-3', which provides the codon alteration resulting in huIL-2(Thr73). The annealing reaction was conducted substantially as disclosed by Walder et al., supra, and the resulting single-stranded DNA bearing the annealed oligonucleotide was transformed directly into S. cerevisiae XV2181 by conventional methods. Following transformation, approximately 100 yeast colonies were picked, pooled, and plasmid DNA isolated. This was used to transform E. coli RR1, and approximately 100 E. coli transformants were transferred to nitrocellulose filters and probed by hybridization with the foregoing mutagenic oligonucleotide (radiolabelled with $^{32}$P) at 37° C. overnight in 6XSSC, followed by washing at 55° C. in 6XSSC. One positive hybridizing clone was identified and its plasmid DNA isolated (this vector was designated pIXY188) and used to transform XV2181. The resulting transformed strain was grown in culture under conditions enabling derepression of the ADH2 promoter. The resulting huIL-2 exhibited wild-type biological activity as well as an increase of about 5,000–10,000 daltons in molecular weight due to glycosylation.

An alternative approach to adding glycosylation sites involves adding an N-terminal leader to the huIL-2 sequence which encodes two additional N-glycosylation sites. This version was constructed by ligating the following oligonucleotide to an HgiA1- and StuI-cut huIL-2 cDNA and an Asp718- and StuI-cut derivative of the yeast expression vector pIXY120:

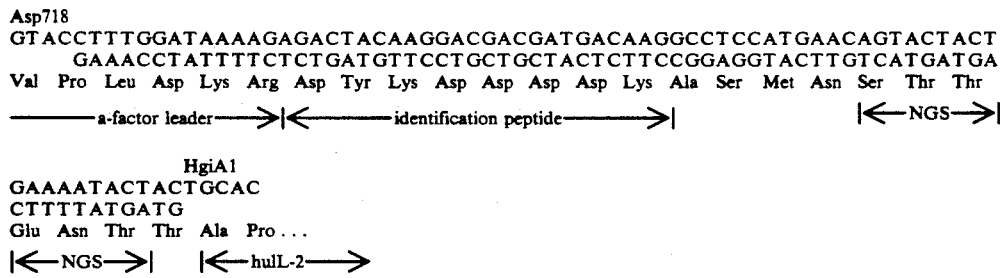

This oligonucleotide includes an identification octapeptide which is capable of being identified by specific antibody (see U.S. Pat. No. 4,703,004) and two N-linked glycosylation sites (NGS). Expression of the resulting construct in *S. cerevisae* XV2181 provided a heavily glycosylated huIL-2 molecule which retained receptor-binding activity. This molecule was conjugated to fluorescein as described in Example 2 for rmuIL-4, above, and used to detect the presence of high-affinity IL-2 receptors on various cell types.

What is claimed is:

1. A ligand reagent consisting essentially of a hyperglycosylated recombinant cytokine conjugated to a functional moiety via an oligosaccharide residue wherein said cytokine is capable of binding to a cytokine receptor.

2. The ligand reagent according to claim 1, wherein the functional moiety is conjugated to the oligosaccharide residue via a biotin or avidin group.

3. The ligand reagent according to claim 1, wherein the functional moiety comprises a member selected from the group consisting of radiolabels, fluorophores, chromophores, solid substrates, magnetic particles, toxins, and enzymes.

4. The ligand reagent according to claim 2, wherein the cytokine is a lymphokine.

5. The ligand reagent according to claim 3, wherein the cytokine is a lymphokine.

6. The ligand reagent according to claim 1, wherein the hyperglycosylated cytokine is a recombinant analog of a native cytokine, produced by expression in yeast of a DNA sequence encoding an amino acid sequence having one or more N-linked glycosylation sites not present in the amino acid sequence of the native cytokine.

7. The ligand reagent according to claim 1, wherein the functional moiety comprises a fluorescein group.

8. The ligand reagent according to claim 1, wherein the cytokine is conjugated to a solid substrate.

9. The ligand reagent according to claim 2, wherein the cytokine is conjugated to a solid substrate.

10. A ligand reagent consisting essentially of a hyperglycosylated recombinant cytokine expressed in yeast conjugated to a functional moiety via an oligosaccharide residue wherein said cytokine is capable of binding to a cytokine receptor.

* * * * *